(12) United States Patent
Broeker

(10) Patent No.: US 10,071,194 B2
(45) Date of Patent: Sep. 11, 2018

(54) DEVICE FOR EXTRA-CORPORAL BLOOD TREATMENT WITH LEAKAGE SENSOR

(71) Applicant: B. Braun Avitum AG, Melsungen (DE)

(72) Inventor: Bjoern Broeker, Staufenberg (DE)

(73) Assignee: B. Braun Avitum AG, Melsungen (DE)

( * ) Notice: Subject to any disclaimer, the term of this patent is extended or adjusted under 35 U.S.C. 154(b) by 630 days.

(21) Appl. No.: 13/864,682

(22) Filed: Apr. 17, 2013

(65) Prior Publication Data

US 2013/0276908 A1    Oct. 24, 2013

(30) Foreign Application Priority Data

Apr. 20, 2012 (DE) ........................ 10 2012 103 504

(51) Int. Cl.
*A61M 1/14* (2006.01)
*A61M 1/36* (2006.01)

(52) U.S. Cl.
CPC .............. *A61M 1/367* (2013.01); *A61M 1/14* (2013.01); *A61M 1/3656* (2014.02); *A61M 2205/15* (2013.01); *A61M 2205/18* (2013.01); *A61M 2209/084* (2013.01); *Y10T 137/1842* (2015.04)

(58) Field of Classification Search
None
See application file for complete search history.

(56) References Cited

U.S. PATENT DOCUMENTS

| 5,674,390 A | 10/1997 | Matthews et al. |
| 5,863,421 A | 1/1999 | Peter et al. |
| 2003/0126910 A1* | 7/2003 | Burbank ........................ 73/40 |
| 2004/0084358 A1* | 5/2004 | O'Mahony et al. ............ 210/94 |
| 2009/0107335 A1 | 4/2009 | Wilt et al. |
| 2011/0230753 A1 | 9/2011 | Mahon et al. |

(Continued)

FOREIGN PATENT DOCUMENTS

| DE | 196 05 260 | 11/1996 |
| DE | 10 2009 051993 | 5/2011 |

(Continued)

OTHER PUBLICATIONS

German Search Report for DE 10 2012 103 504.0 dated Nov. 30, 2011.

(Continued)

*Primary Examiner* — Bobby Ramdhanie
*Assistant Examiner* — Jonathan Peo
(74) *Attorney, Agent, or Firm* — RatnerPrestia

(57) ABSTRACT

The invention concerns a device for extra-corporal blood treatment, including an extra-corporal blood circulation for the pumping of blood, where individual components of the extra-corporal blood circulation are inside and outside of a casing of the device, and a base socket is attached below the casing, which includes a collection trough in which liquids leaking inside the casing can be collected. The device has a sensor with which the presence of liquid within the collection trough is measurable. The device includes receptacle resources for the reception of leaking liquids occurring outside of the casing, where the receptacle resources are developed so that, above a specified quantity, they route leaking liquids into the collection trough.

17 Claims, 6 Drawing Sheets

(56) References Cited

U.S. PATENT DOCUMENTS

2011/0315237 A1* 12/2011 Jenkins .................. 137/312
2011/0315611 A1* 12/2011 Fulkerson et al. ........... 210/96.2

FOREIGN PATENT DOCUMENTS

| | | |
|---|---|---|
| DE | 102009051993 A1 * | 5/2011 |
| GB | 2 199 436 | 7/1988 |
| GB | 2 272 553 | 5/1994 |
| WO | WO 2004/096322 | 11/2004 |
| WO | WO 2009/090473 | 7/2009 |
| WO | WO 2010/062698 | 6/2010 |
| WO | WO 2011/140268 | 11/2011 |

OTHER PUBLICATIONS

European Search Report for EP 13 16 0455 dated Jun. 11, 2013.
Translation of Chinese Exam Report for CN 2013101341494 with Search Report dated Jun. 3, 2015.

* cited by examiner

DEVICE FOR EXTRA-CORPORAL BLOOD TREATMENT WITH LEAKAGE SENSOR

CROSS REFERENCE TO RELATED APPLICATIONS

This application claims priority to German Application No. DE 10 2012 103 504.0 filed Apr. 20, 2012, the contents of such application being incorporated by reference herein.

FIELD OF THE INVENTION

The invention concerns a device for extra-corporal blood treatment, including at least an extra-corporal blood circulation for the pumping of blood. The device can furthermore include a dialyzer for the substance exchange between the blood and a dialysate, and an hydraulic system for the appropriation of the dialysate.

DESCRIPTION OF THE RELATED ART

In the case of such dialysis devices, leakage in the extra-corporal hose system, or in the hose connection in the balancing circuit, with occurrence during therapy can lead to ultra-filtration deviations and loss of blood, which can have serious results for the patient under certain circumstances. The sealing test of the hydraulic circuit and of the extra-corporal blood circulation is realized with most devices in an one-time way, or cyclically through a pressure test, however, a continuous monitoring during all therapy phases is very difficult. Therefore corresponding sensors are often employed for the determination of leakage.

Since there can be several possible causes for lack of sealing, several sensors are usually necessary in order to determine the individual leakage. For example, it is known to employ a total of three sensors for the detection of leakage, with which one sensor is located in the device interior, one in the casing of the DF filter and one in the collecting conduit for liquids on a front panel in each case.

However, it is also possible to collect all possibly occurring leaking liquids from different sources in a collection container in the lower area of the dialysis device, and to provide only one sensor which then measures the filling level of the collection container and, for example, triggers an alarm above a pre-determined filling level. DE 196 05 260 B4 describes, for example, a leakage sensor on the trough-shaped base of a dialysis device. Fluids, such as blood, water or dialysate, which can flow from different modules because of leakage, are collected in a collecting reservoir on the base of the device. Such leak flows can flow over any path.

The base of the casing of the device is not horizontally level in this case, such as for instance is known from the oil pan of an engine, so that the collection of the fluid is facilitated. The base of the device can have the form of a bowl or some other suitable contour, which provides a lower collecting reservoir. A fluid sensor is then arranged near the collecting reservoir, in order to indicate the occurrence of fluid in the collecting reservoir. If fluid is detected by the sensor, the operating system or the protection system triggers an alarm in order to alert the user, using an acoustic or visual signal, and the device is checked for leakage. U.S. Pat. No. 5,674,390 manifests a similar implementation form of a collection trough, where a sensor is attached to the trough at the deepest point.

Furthermore, WO 2004/096322 A1 manifests a dialysis device with a funnel-shaped collection trough in the base area, into which all leaking liquids run and contact the two sensors which are attached at different heights. The lower sensor then detects a lower filling level limit of leaking liquids, while the second sensor measures a higher filling level. In addition, WO 2009/090473 A1 describes a leakage sensor which is displaced from the device interior to outside.

If no conduit is employed on a front panel, rather a central collection trough in the base socket of the device, drops can also reach the respective sensor from the concentrate canisters. Therefore a too-high sensitivity of the sensors employed is counter-productive, since otherwise these would trigger an alarm, due only to certain quantities of concentrate which do not yet represent any hazard, without there being any leakage in the device, because these concentrate drops could also occur, for example, with the connection of canisters to the dialysis device.

In the case of leaks, the liquid must furthermore be removed again, so that the collecting tank is preferably easily accessible where liquids can be removed easily by the personnel.

SUMMARY OF THE INVENTION

The task of the invention is therefore to provide a device for extra-corporal blood treatment, where leaking liquids from different sources are capable of being detected securely, however, where small quantities of visible leaking liquids, which do not represent any hazard, should be easily removable before an alarm is triggered.

Invention-related, this task is solved by a device in accordance with the independent Claim 1. Further advantageous features of the device result from the subordinate Claims 2-16.

The invention-related device for the extra-corporal blood treatment includes at least one extra-corporal blood circulation for the pumping of blood. The individual components of this extra-corporal blood circulation in this case are located inside and outside of a casing of the device, where a base socket is attached below the casing, which indicates a collection trough in which liquids leaking within the casing are collectible. The device indicates a sensor, with which the existence of liquid within the collection trough is measurable at least. Invention-related, the device indicates further receptacle resources for the reception of leaking liquids occurring outside of the casing, where these receptacle resources are developed so that, above a specified quantity, they transfer at least a part of the leaking liquids outside of the casing into the collection trough.

This structure has the result that leaking liquids which arise from components in the interior of the device are collected directly in a collection trough, and a corresponding sensor is implemented so that it can detect the existence of liquid in the collection trough. This signal can be correspondingly evaluated by a control and evaluation unit, where, for example, an alarm is generated and the treatment is interrupted. As an extension, leaking liquids which arise outside of the casing are transferred into the collection trough delayed only. They would therefore not lead to the triggering of an alarm until above a pre-determined quantity. The invention-related device for extra-corporal blood treatment thus differentiates between internal leaks, which are routed into the collection trough without delay to the sensor, and external leaks which, for example, are first collected visibly on the base socket before being able to reach the sensor.

In this way, it is guaranteed that only relevant amounts of liquid are detected by the sensor, however, in spite of different sensitivity requirements, only one sensor is required in this case.

This has the advantage that harmless quantities of leaking liquid can be removed by the operating personnel beforehand, without its having to result in an alarm. Preferably, the receptacle resources in which the liquids occurring outside of the casing are collected up to a pre-determined quantity value are visible outside of the casing and accessible. Thus the operating personnel can see that liquids leaking externally collect and, for example, can simply wipe them off without the therapy being disturbed by an alarm. However, if the operating personnel do not notice that leaking liquids from outside components collect, or if it involves such large quantities that a large-scale leakage is assumed, these are routed into the collection trough. The control unit which receives the sensor signal will then sound an alarm and interrupt the treatment.

Typically the device for extra-corporal blood treatment, as well as the extra-corporal blood circulation for the pumping of blood, also includes an hydraulic system for the appropriation of dialyzing liquid, where individual components of the hydraulic system can also be inside and outside of the casing of the device. For example, the hydraulic system includes at least one storage tank or canister, which contains a medium for the preparation of the dialysate. In this case, at least this storage tank can be located outside of the casing, but also hose lines of the hydraulic system can be arranged outside of the casing. Often it then occurs that drops form with collection on such hose lines and storage tanks, which drop or flow down on the front panel of the casing.

The blood hose system is typically mounted on the front of the device and filled with liquid for the preparation of the treatment. Also drops can form at the connection points of the blood hose system and run down on the front panel of the device.

In particular, with smaller quantities, these can simply be wiped off during usual surface cleaning of the device.

In an implementation form of the invention, the base socket of the device extends at least beyond the casing on the front panel of the casing. In this front area of the base socket, which is visible and accessible from outside, parts of the collection trough, as well as the sensor and/or the receptacle resources for the delayed supply of external leaking liquids, can then be arranged in the collection trough. Effectively, the sensor is in the lower area of the collection trough.

As receptacle resources in the front area of the base socket located outside of the casing, for example, at least one conduit open above can be provided, which has a connection to the collection trough, where the connection between the conduit and the collection trough is designed so that the leaking liquids collected in the conduit flow into the collection trough only above a specified quantity. The volume of the conduit or the connection to the collection trough are selected correspondingly, in order to achieve the required delay. The connection between the conduit and the collection trough can be realized in different ways, where a cross-piece between the conduit and the collection trough has proved a simple and effective means. The height of the cross-piece then lies below the edge of the conduit, so that liquid collects in the conduit for so long until the level reaches the top edge of the cross-piece. Then so much liquid flows over the cross-piece into the collection trough, that the level is again located exactly at the top edge of the cross-piece.

In the described design example with a conduit as receptacle resource and a cross-piece for the volume regulation, the specified quantity of leaking liquid, where this is transferred to the collection trough, thus results from the volume of collected liquid. However, the quantity can also be defined differently. For example, implementation designs are conceivable where externally occurring leaking liquids collect for so long at or on a plate, until a pre-determined weight is reached and the plate lowers or tilts over in order to then transfer the liquid to the collection trough. In this case, the relevant quantity for the transfer of the liquid would be defined by the weight of the liquid.

Furthermore, instead of the collection of external leaking liquid in a container, other types of receptacle resources could also be employed in order to achieve the required delay. For example, it would be possible to collect external leaking liquid first in a sponge-like material, which is selected so that the leaking liquid drops again from the material if a pre-determined saturation point is reached. In this case, the relevant quantity would be again defined over the volume or the weight of the liquid, according to implementation design. The liquid could then be removed manually, for example, by squeezing the sponge material.

A solution with a conduit in the base socket therefore certainly represents a preferred implementation form of the invention, however. The invention is not limited to this form of receptacle resource. Also the relevant quantity for the transfer of liquid into the collection trough with sensor is not limited according to the volume or weight of the liquid, rather it depends on the selected receptacle resources. The specified quantity of liquid with which this is transferred to the collection trough can also be freely optional, so that, for example, it can be adjusted by the operating personnel. This can be achieved in particular by movable component parts if, for example, the described cross-piece can be changed in height.

In a design example of the invention, the base socket further indicates resources for the supply of leaking liquids to the receptacle resources in the area outside of the casing. In this case, it can, for example, involve correspondingly sloping surfaces on which drops flow off in the direction of a conduit.

In a further design example of the invention, the collection trough likewise extends out beyond the casing, and the sensor is positioned in this area of the collection trough located outside of the casing. This has the advantage that both the collection trough, as well as the sensor, are accessible from externally and are capable of being cleaned simply. In particular, no tool is required for cleaning the sensor. Leaking liquids from the interior of the casing are then collected internally, but they are then routed externally to the sensor if the deepest point of the collection trough is located there.

In this case, however, it must be guaranteed that, by means of a corresponding implementation of the base socket, only leaking liquids are routed directly into the collection trough from the interior of the casing, while leaking liquids from the front panel of the device are collected first in the receptacle resources selected in each case, and do not flow directly into the collection trough. This can be achieved, for example, in that the area of the collection trough located outside of the casing indicates a removable cover. Thus externally no liquid can drop into the collection trough from above, but the operating personnel have nevertheless easy access to the collection trough and the sensor by removing or folding up the cover if required.

In a design example of the invention, the casing is developed further so that leaking liquids occurring outside of the casing are routed to the receptacle resources by means of capillary action. Here, the surface of the front panel of the casing can, for example, indicate several stamped grooves.

In addition, the sensor and/or an evaluation unit of the device connected to the sensor can be developed so that, with the identification of liquids in the collection trough, two or more liquids from the blood group, dialysis liquid, concentrate, disinfection liquid and water can be specifically differentiated between. For example, this differentiation of the liquids can be feasible on color-selective basis.

Furthermore, it is preferably planned that the extra-corporal blood circulation includes a blood hose system and the hydraulic system a dialysis liquid flow system, and that the device indicates a control and/or control-check unit, through which, with identification of leakage by means of the sensor, an automatic sealing verification of the dialysis liquid flow system and/or the blood hose system is capable of initiation.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
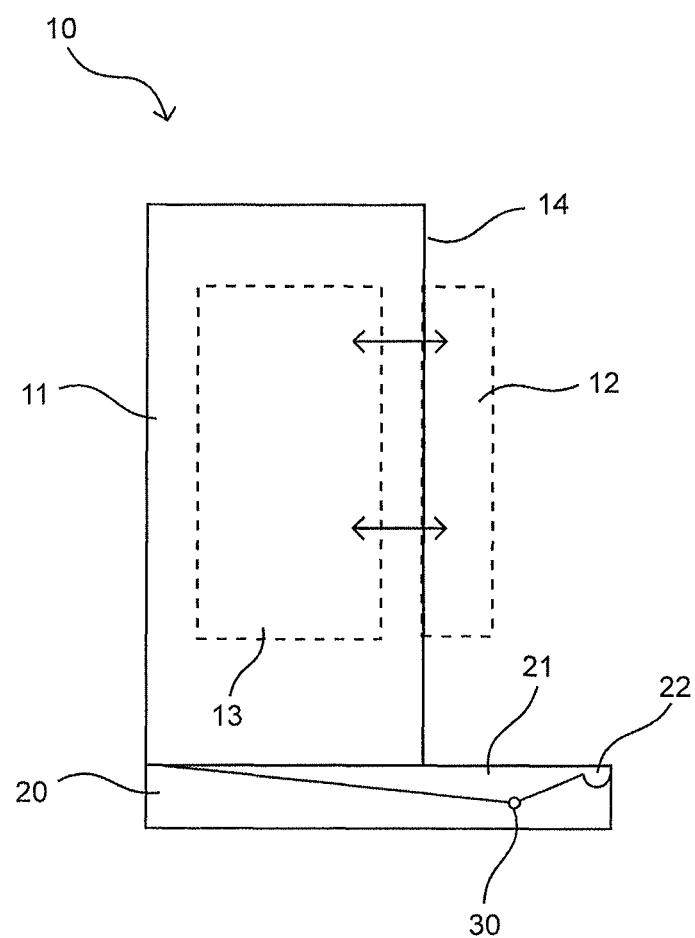
FIG. 1 Indicates a schematic representation of the components of a dialysis device.

In FIG. 1 the components important for the invention and/or areas of a dialysis device 10 are represented schematically, where the device can be implemented as a haemofiltration (HF), a haemodialysis (HD) or a combination of both dialysis procedures in the form of a haemodiafiltration (HDF). The dialysis device 10 in this case includes at least one extra-corporal blood circulation for the pumping of blood, a dialyzer for the substance exchange between the blood, and a dialysate and a hydraulic system for the appropriation of the dialysate and the dialysis solution in the dialyzer. The blood circulation in this case consists of a blood module of the dialysis device and a blood hose system, which are usually implemented as one-off articles. The blood module can include at least addition points for medication, pressure gauges, a blood pump and sensors for the identification of air bubbles in the hose system. The dialyzer indicates a semi-permeable membrane over which the substance exchange is implemented between the blood and the dialysate, where the dialyzer is switched into the blood circulation.

The hydraulic system (balancing circuit) likewise includes a hose system, a filter and at least one storage tank which contains a medium for the preparation of the dialysate.

It can involve, for example, water, bi-carbonate and/or lactate in this case. The individual components of the blood circulation and the hydraulic system are not represented in detail in this case, rather FIG. 1 indicates schematically only that some components and parts of the extra-corporal blood circulation and the hydraulic system are located within the casing of the device, where these components are represented in dashed line and are marked generally with the reference digit 13.

Other components of the extra-corporal blood circulation and the hydraulic system are in contrast arranged outside of the casing 11, and are also represented dashed and identified with the reference digit 12. These external components are located in particular at the front panel 14 of the dialysis device 10 in this case. Typically, it involves hoses and connections in this case, but also canisters in which media for the appropriation of the dialysate are located.

Below the casing 11 is arranged a base socket 20, in which a collection trough 21 is located. The base socket 20 can consist of plastic and be formed in one piece or assembled from several parts. The collection trough 21 in this case is formed such that leaking liquids which could discharge from the inner components 13 of the dialysis device 10 are held in the base area of the device 10 and collected. In the design example of the invention represented in FIG. 1, the base socket 20, together with the collection trough 21, extends out beyond the casing 11. Preferably, this is at least the case on the front panel 14 of the device, so that leaking liquids, which can arise from the external components 12 of the blood circulation and/or the hydraulic system in this front area 14, are also collected in the base socket 20. A conduit 22 is provided for this purpose at the edge of the base socket 20. The structure of such a base socket 20 with conduit 22 is displayed in FIGS. 2 to 4 in detail.

Figure 2:
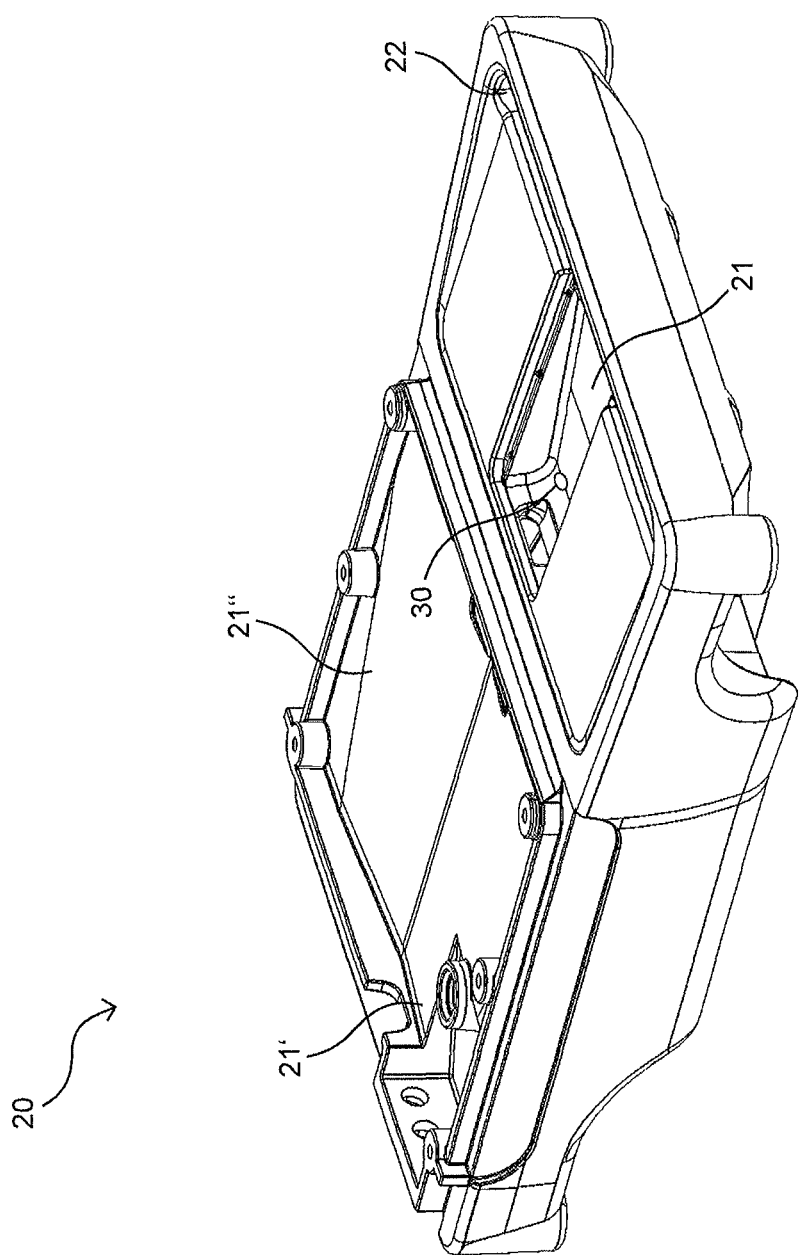
FIG. 2 Indicates a three-dimensional view of an design example of a base socket with leakage sensor.
Figure 3:
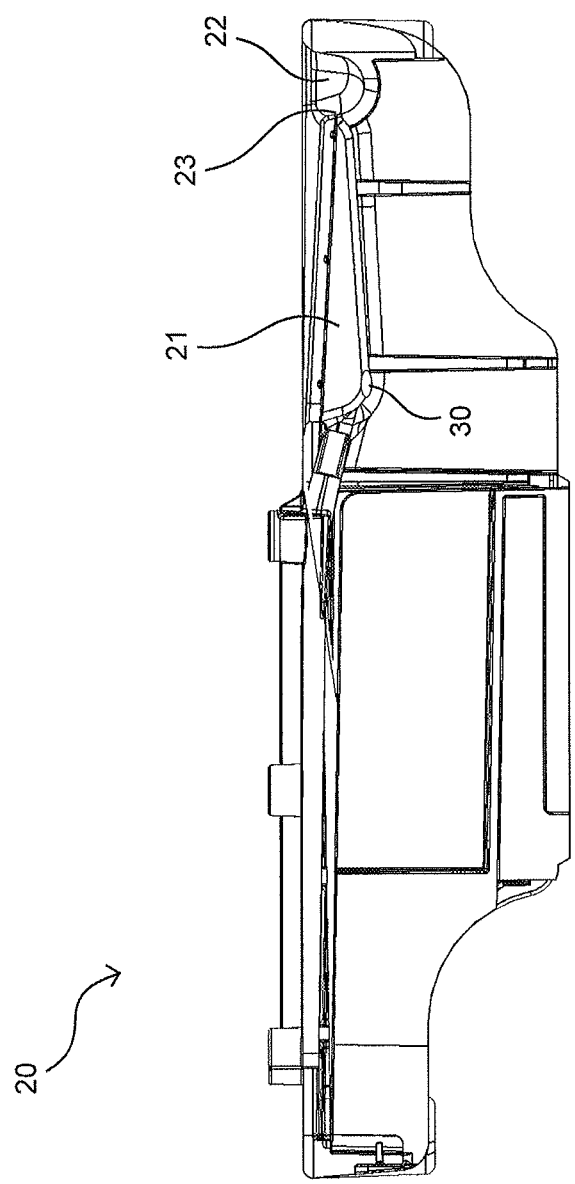
FIG. 3 Indicates a longitudinal section through a base socket in accordance with FIG. 2.

FIG. 2 indicates a design example of a base socket 20, where the deepest point of the collection trough 21 is outside of the non-represented casing 11 of the dialysis device 10. The collection trough 21 is not developed as a trough with trough sides formed uniformly concave in this case, rather it indicates two diagonal trough surfaces within the casing 21' and 21", with which liquids which drop onto these trough surfaces are routed into the middle of the device and to the front panel 14.

There, via an air gap, they reach the area of the collection trough 21 in which the sensor 30 is located. The collection trough 21 is thus within the casing as a result of the trough surfaces 21', 21" and the corresponding trough is formed outside of the casing. According to construction design and function, the sensor 30 is preferably attached to the shaped collection trough 21, so that liquid is detected in the lower area of the trough. This is the case in the represented design example outside of the casing. However, it can also be designed so that the deepest point of the trough 21 and the sensor 30 are provided below the casing. In this case, the sensor would no longer be freely accessible, however this implementation could bring other advantages under certain circumstances. The sensor 30 can, for example, detect liquid using an optical method, however, other sensors such as float switches, electric contacts (current measurement) or ultrasonic sections are also conceivable.

At the edge of the external area of the base socket 20 is located conduit 22 which is formed open above, which runs crossways on the front edge of the base socket 20, or can be developed in another way. For example, a U-shaped conduit could be useful, if this runs along the edge of the base socket 20 and thus collects any liquid which flows off externally. Between this conduit 22 and the collection trough 21, the base socket 20 is therefore preferably implemented so that liquids which arise from leakage on the external components of the dialysis device 10 are routed to the conduit 22 and do not flow directly into the collection trough 21. For this purpose, the surface of the base socket 20 is outside of the collection trough 21 and, for example, the conduit 22 is developed correspondingly sloped.

As a result of this implementation and/or contouring technique of the base socket 20, the leaking liquids from the interior of the casing collect directly in the collection trough 21, while possibly leaking liquids from external components of the device 10 are collected in the conduit 22. As can be seen in the section in FIG. 3, a cross-piece 23 is attached between the conduit 22 and the collection trough 21, which basically prevents any connection between these two collection agents.

However, the top edge of the cross-piece 23 lies below the external edge of the conduit 22, so that liquids which collect in conduit 22, above a pre-determined level, flow into the collection trough 21 over the cross-piece 23. The height of the cross-piece 23, together with the volume of the conduit 22, can then be selected so that external leaking liquids above a pre-determined volume are transferred to the collection trough 21 and with that the sensor 30. Preferably this volume is selected so that liquid is routed first from the conduit 22 into the collection trough 21, and thus reaches sensor 30, when more liquid has collected in the conduit 22 than is to be expected under normal operating conditions due to wiping and/or dropping etc.

Figure 4:
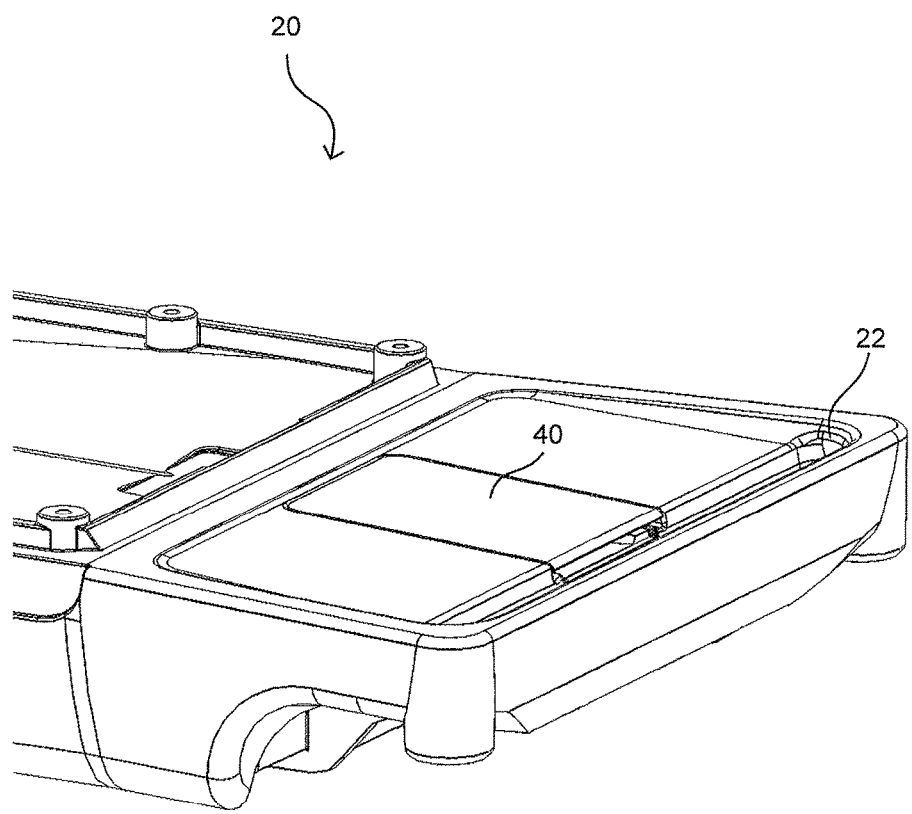
FIG. 4 Indicates a three-dimensional partial view of a base socket with covering.

FIG. 4 indicates the base socket 20 in an implementation form where the collection trough is concealed with a removable cover 40. Also a direct dropping of liquids into the collection trough 21 is prevented by this. Nevertheless, the collection trough 21, and thus also the sensor 30, are easily accessible for the operating personnel, so that, for example, the sensor 30 can also be cleaned easily and without the application of a tool.

As a result of the described structure of the base socket 20, leaking liquids from the external components 12 of the dialysis device 10 reach the collection trough 21 delayed, while leaking liquids from the inner components 13 are collected directly in the collection trough 21, and can be detected by the sensor 30. In this case, the sensor 30 can be developed or connected to an evaluation unit, such that it immediately triggers an alarm with detection of a liquid in the collection trough 21. In this way, the operating personnel are made immediately aware when liquid arrives in the collection trough 21. However, it can also be provided that the sensor 30 triggers an alarm only above a pre-determined liquid level within the collection trough 21, or several level limits are programmed where the sensor triggers different alarms.

Figure 5:
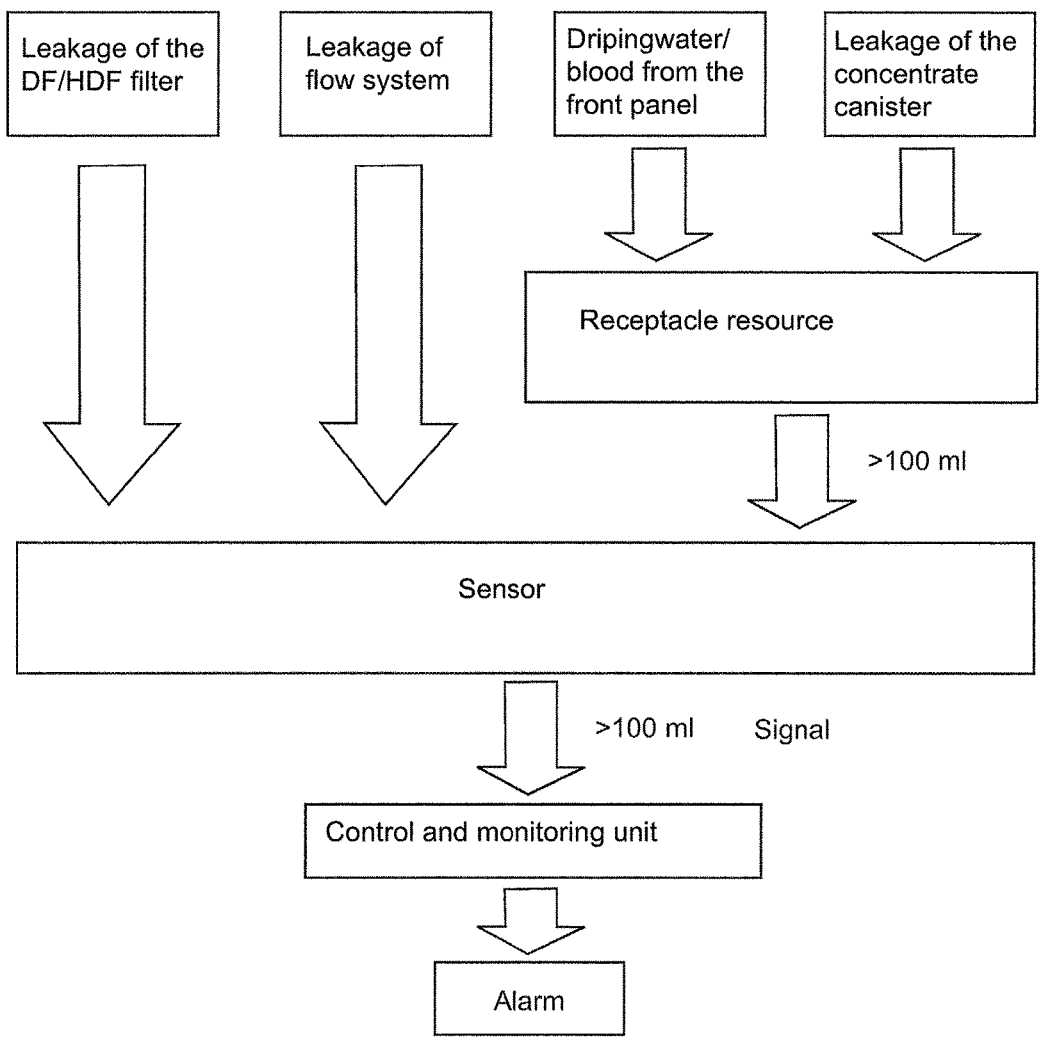
FIG. 5 Indicates a schematic representation of possible sources and the handling of leaking liquids.

FIG. 5 indicates schematically in a diagram the possible sources for leaking liquids and their possible handling through the invention-related device. For example, leaks from DF/HDF filter and/or leaks in the dialysis liquid flow system, can be routed directly to the sensor in the interior of the device, while dripping water or blood from the front panel and/or liquids from the canisters for the dialysate appropriation, are first routed to a receptacle resource.

Figure 6:
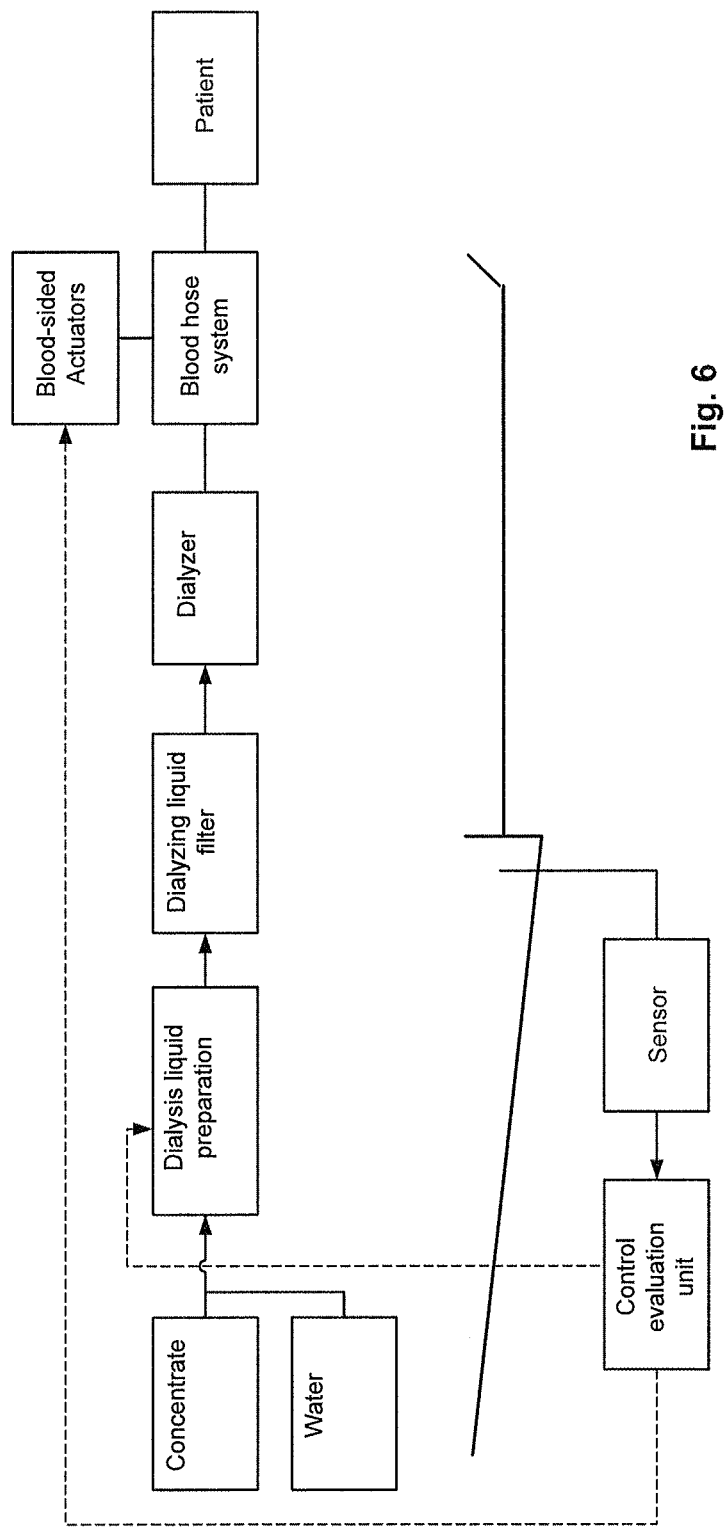
FIG. 6 Indicates a schematic circuit diagram of the dialysis liquid flow circulation and of the extra-corporal blood circulation, with control and display.

These liquids are then also routed further to the sensor above, for example, a quantity of 100 ml. This likewise then triggers an alarm above a total amount of liquid of 100 ml. For this purpose, FIG. 6 indicates a schematic circuit diagram of the dialysis liquid flow circulation and of the extra-corporal blood circulation, with a control and a display.

The control and evaluation unit of the dialysis device reacts to the signals of the sensor 30 with the presence of liquid, for example, through initiation of a corresponding recommendation to the operator if the device cannot identify the cause of the liquid. However, verification mechanisms can also be provided in order to determine the cause of the leakage, and to display it to the operator. If the user removes the liquid through wiping off and/or suctioning, and is certain in this case that the cause is not a device defect, the treatment can be continued. Also conceivable would be the start of an automatic sealing test of the hydraulic circuit and/or the blood hose system (pressure retention test), in order to check the correct function of the device.

In a design example of the invention, the sensor 30 is implemented as an optical sensor which detects a liquid by means of optical boundary-surface reflection. Optoelectronic sensors can also be employed. Alternatively, the sensor can also be realized on capacitive basis and at the same time form the collection trough 21.

In a design example of the invention, color-selective sensors can be employed in addition. Thus, for example, different leaking liquids, such as water or blood, can be differentiated between specifically, where different protection objectives, such as ultra-filtration deviations and losses of blood could be prioritized differently.

The leaking liquids can be routed further to the different collecting tanks by a pre-determined structuring of the casing 11. In particular, the front panel 14 of the casing 11 can be developed, for example, so that a directed liquid routing is implemented through capillary action.

Here, the surface of the front panel 14 of the casing 11 can indicate several stamped grooves, or the columns of the casing 11 can have a correspondingly small width.

Furthermore, the adhesion of the liquids to the surface of the casing 11 can be minimized, where the surface is equipped with a lotus effect. Thus liquid forms bubbles more easily and flows directly into the respective collecting tank.

The invention claimed is:

1. A device for extra-corporal blood treatment, the device comprising:
   a casing;
   extra-corporal blood circulation components located inside and outside of the casing;
   a base socket attached below the casing, the base socket including a collection trough configured to collect internal leaking liquids occurring within the casing directly;
   receptacle resources, including a conduit, the receptacle resources positioned below the components located outside of the casing, at least a portion of the receptacle resources positioned over the collection trough to directly receive only external leaking liquids occurring outside of the casing, wherein the receptacle resources are configured to direct the external leaking liquids into the conduit, and wherein the conduit is configured to sequester the external leaking liquids from the collection trough until the external leaking liquids are above a specified quantity, and above the specified quantity, the conduit is further configured to route at least a part of the sequestered external leaking liquids into the collection trough; and
   a sensor with which at least the presence of liquid is measurable within the collection trough.

2. The device according to claim 1, further comprising:
   hydraulic system components for the appropriation of dialyzing liquid located inside and outside of the casing.

3. The device according to claim 1, wherein the receptacle resources are visible and accessible from outside the casing.

4. The device according to claim 1, wherein the hydraulic system components include at least one storage tank located outside the casing which contains a medium for the preparation of a dialysate.

5. The device according to claim 1, wherein the casing includes a front panel and the base socket includes a portion extending beyond the front panel of the casing.

6. The device according to claim 5, wherein the base socket includes the receptacle resources and wherein a front area of the base socket is located outside of the casing as the receptacle resources, and wherein the conduit is further configured to open upwards and to provide a connection to the collection trough.

7. The device according to claim 6, further comprising:
a cross-piece attached between the conduit and the collection trough, whose height lies below the edge of the conduit.

8. The device according to claim 5, wherein the portion of the base socket extending beyond the front panel provides resources for the supply of the external leaking liquids to the receptacle resources.

9. The device according to claim 5, wherein the sensor is positioned in the collection trough in the portion of the base socket extending beyond the front panel of the casing.

10. The device according to claim 1, wherein the sensor is located at the deepest point of the collection trough.

11. The device according to claim 5, further comprising:
a removable cover for the portion of the base socket extending beyond the front panel of the casing.

12. The device according to claim 1, wherein the casing is configured such that the external leaking liquids occurring outside of the casing are routed to the receptacle resources by means of capillary action.

13. The device according to claim 12, wherein the casing includes a front panel and wherein the front panel of the casing includes several stamped grooves.

14. The device according to claim 1, wherein the sensor and/or an evaluation unit of the device connected to the sensor are configured such that, with the identification of liquids in the collection trough, two or more liquids from the group of blood, dialysis liquid, concentrate, disinfection liquid, or water can be specifically differentiated between.

15. The device according to claim 14, wherein the differentiation of the liquids is based on color-selection.

16. The device according to claim 2, wherein the extracorporal blood circulation components include a blood hose system and the hydraulic system components include a dialysis liquid flow system and wherein the device further comprises:
a control and/or control-check unit, through which, with identification of leakage by means of the sensor, an automatic sealing verification of the dialysis liquid flow system and/or the blood hose system is capable of being initiated.

17. The device according to claim 2, wherein the receptacle resources are visible and accessible from outside the casing.

* * * * *